US00PP35071P2

(12) United States Plant Patent
Bergman

(10) Patent No.: US PP35,071 P2
(45) Date of Patent: Mar. 28, 2023

(54) ***LANTANA* PLANT NAMED 'LANZ0045'**

(50) Latin Name: ***Lantana camara* L.**
Varietal Denomination: LANZ0045

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 28 days.

(21) Appl. No.: 17/875,546

(22) Filed: Jul. 28, 2022

(51) Int. Cl.
*A01H 5/02* (2018.01)
*A01H 6/86* (2018.01)

(52) U.S. Cl.
USPC ..... Plt./227
CPC ..... *A01H 6/86* (2018.05)

(58) Field of Classification Search
USPC ..... Plt./227
CPC ..... A01H 5/02
See application file for complete search history.

*Primary Examiner* — Kent L Bell
(74) *Attorney, Agent, or Firm* — Dale Skalla

(57) ABSTRACT

A new *Lantana* plant named 'LANZ0045' having medium size mature dark cherry-red flower color, excellent flower production, medium size plant growth and uniform dense semi-spreading habit with medium-small sized dark green foliage.

1 Drawing Sheet

Latin name of the genus and species of the plant claimed: *Lantana camara* L.

Varietal denomination: 'LANZ0045'.

BACKGROUND OF THE NEW PLANT

The present invention comprises a new *Lantana*, botanically known as *Lantana camara* L., and hereinafter referred to by the variety name 'LANZ0045'.

'LANZ0045' is a product of a planned breeding program in Gilroy, Calif. The new cultivar 'LANZ0045' has medium size mature dark cherry-red flower color, excellent flower production, medium size plant growth and uniform dense semi-spreading habit with medium-small sized dark green foliage.

The new *Lantana* cultivar, 'LANZ0045', is the result of open hybridization made in an outdoor field in Gilroy, Calif. in the summer of 2016. The female parent of the new cultivar is the commercially available *Lantana camara* variety 'Little Lucky Hot Pink', U.S. Pat. No. 24,555, characterized by its dark cherry red inflorescences, medium green-colored foliage and vigorous spreading growth habit. 'LANZ0045' differs from 'Little Lucky Hot Pink' having darker cherry-red flower color, especially under lower light conditions, and smaller plant size. The male parent of the new cultivar is not known.

The seed was sown in August 2017 in a controlled greenhouse environment in Gilroy, Calif., and 'LANZ0045' was selected as one flowering plant within the progeny of the stated cross in November 2017.

The first act of asexual reproduction of 'LANZ0045' was accomplished when vegetative stem cuttings were propagated from the initial selection in February 2018, in Gilroy, Calif.

BRIEF SUMMARY OF INVENTION

Horticultural examination of plants grown from cuttings of the plant initiated in February 2018, in Gilroy, Calif., and continuing thereafter, has demonstrated that the combination of characteristics as herein disclosed for 'LANZ0045' are firmly fixed and are retained through successive generations of asexual reproduction.

'LANZ0045' has not been observed under all possible environmental conditions. The phenotype may vary significantly with variations in environment such as temperature, light intensity, and day length.

A Plant Breeder's Right for this cultivar has not been applied for. 'LANZ0045' has not been made publicly available prior to the effective filing date of this application, notwithstanding any disclosure that may have been made less than one year prior to the effective filing data of this application by the inventor or another who obtained 'LANZ0045' directly from the inventor.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0045' with colors being as true as possible with an illustration of this type.

Figure 1:
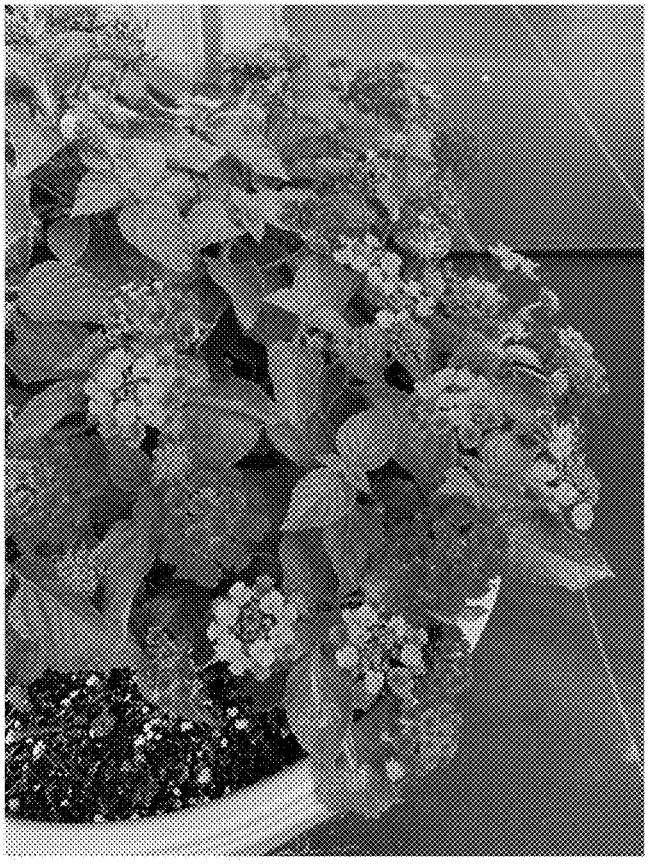
Figure 2:
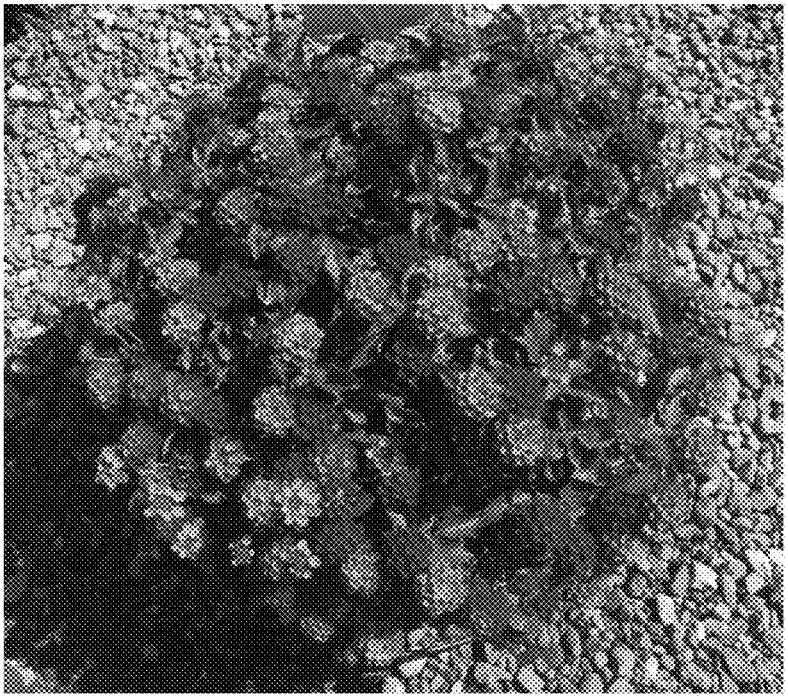

The photographic drawings show in FIG. 1 a close view of inflorescences taken in Monroeville, N.J. in July 2020, and in FIG. 2 a whole flowering plant taken in Gilroy, Calif. in August 2021.

DETAILED BOTANICAL DESCRIPTION

The plant descriptions and measurements were taken in Gilroy, Calif. in June 2022. The plants were approximately 3 months old and were growing in 14 inch pots, three plants per pot, in a greenhouse.

Color references are made to The Royal Horticultural Society Colour Chart (RHS) 2001.

TABLE 1

DIFFERENCES BETWEEN THE NEW VARIETY 'LANZ0045' AND A MOST SIMILAR VARIETY

| Traits (for example) | 'LANZ0045' | 'Bante Cheriasun', U.S. Plant Pat. No. 19,264 |
|---|---|---|
| Plant habit: | Smaller plant size | Larger plant size |
| Flower color: | Flower color more cherry red | Flower color more cherry pink |
| Seed set: | Lower seed set | More seed set |

Plant:

*Form, growth and habit.*—Semi-woody, grown as an annual or perennial; vigorous semi-spreading habit; very well branched.

*Plant height.*—15 cm.

*Plant height* (*inflorescence included*).—17 cm.

*Plant width.*—21 cm.

Foilage:

*Type.*—Opposite.

*Immature, leaf color, upper surface.*—Closest to RHS 137A.

*Lower surface.*—Closest to RHS 137C.

*Mature, leaf color, upper surface.*—RHS 139A.

*Lower surface.*—Closest to RHS 138A.

*Length.*—4.5-5.7 cm.

*Width.*—2.8-4.0 cm.

*Shape.*—Ovate.

*Base shape.*—Rounded to truncate.

*Apex shape.*—Acute.

*Margin.*—Serrate.

*Texture, upper surface.*—Hairy.

*Texture, lower surface.*—Hairy.

*Pattern of veining.*—Pinnate.

*Petioles color.*—RHS 139C.

*Petioles length.*—1.2-1.7 cm.

*Diameter of petiole.*—01.5 cm.

*Texture* (*upper and lower surface*).—Very short hairs.

Stem:

*Color of stem.*—RHS 138B.

*Length of stem.*—7.0-14.0 cm.

*Diameter.*—0.2-0.3 cm.

*Length of internodes.*—1.3-2.6 cm.

*Texture.*—Some hairs.

Inflorescence:

*Type.*—Umbel like, flattened semi-sphere the florets are sessile on an ovate receptacle.

*Blooming habit.*—Flowers continuously from spring through fall.

*Number of open flowers per inflorescence.*—About 27.

*Quantity of inflorescences per plant.*—About 30.

*Lastingness of individual blooms on the plant.*—About 3 weeks (depending on temperatures).

*Fragrance.*—Slightly spicy.

*Umbel horizontal diameter.*—4.0-4.2 cm.

*Umbel vertical height.*—2.1-2.4 cm.

*Peduncle color.*—RHS 138A.

*Length of peduncle.*—2.2-5.8 cm.

*Peduncle diameter.*—0.15-2.0 cm.

*Texture.*—Some hairs.

Flower:

*Floret form.*—Corolla salver-shaped to shallow cup-shaped, with a relatively long tube at the base; each flower subtended by a single bract.

*Length of floret.*—1.8 cm.

*Width of floret.*—1.1 cm.

*Depth of floret.*—0.9 cm.

*Young floret, color upper surface.*—RHS 15A with overtones of RHS 168B.

*Young floret, color lower surface.*—RHS 15D with tones of RHS 181B.

*Mid age floret, color upper surface.*—Closest to RHS 34A with tones of RHS 179B.

*Mid age floret, color lower surface.*—RHS 184C and RHS 159C.

*Mature florets, color upper surface.*—RHS 53A.

*Mature floret, color lower surface.*—RHS 187D and RHS 158D.

*Apex shape.*—Rounded.

*Degree of lobation.*—Moderate.

*Margin.*—Entire.

*Base.*—Fused.

*Texture, upper surface.*—Smooth.

*Lower surface.*—Smooth.

*Tube, color outer surface.*—Closest to RHS 186A.

*Tube, color inner surface.*—Closest to RHS 186C.

*Tube, length.*—1.0 cm.

*Tube, diameter* (*at opening*).—0.15 cm.

*Tube, texture outer surface.*—Smooth.

*Inner surface.*—Very small hairs.

Bud (just before opening):

*Color.*—RHS 35A.

*Length.*—0.9 cm.

*Width.*—0.3 cm at the apex.

*Shape.*—Tubular with a flared apex.

Bract:

*Color.*—RHS 137C.

*Length.*—0.7-1.1 cm.

*Diameter.*—0.2 cm.

*Texture, upper surface.*—Small hairs.

*Lower surface.*—Small hairs.

Calyx:

*Number of sepals.*—5, fused sepals forming a short tube around the base of the floret.

*Color of sepals.*—RHS 142D.

*Length of sepals.*—0.2 cm.

*Width of sepals.*—0.2 cm.

*Apex shape.*—Obtuse.

*Apex margins.*—Entire.

*Texture, outer surface.*—Small hairs.

*Inner surface.*—Smooth.

Reproductive organs:

*Gynoecium.*—

*Pistil quantity.*—One.

*Length.*—0.4 cm.

*Style color.*—RHS 150D.

*Style length.*—0.2 cm.

*Stigma color.*—RHS 144B.

*Ovary color.*—RHS 144A.

*Ovary length.*—0.1 cm.

*Ovary diameter.*—0.1 cm.

*Androecium.*—

*Stamen quantity.*—4.

*Color of filaments.*—RHS 159D.

*Length filaments.*—0.05 cm.

*Anther color.*—RHS 4C.

*Length of anthers.*—0.1 cm.
*Color of pollen.*—RHS 4D.
*Pollen amount.*—Scant.
*Fertility/seed set.*—Moderate.
*Disease/pest resistance.*—Has not been determined to date.

What is claimed is:

1. A new and distinct variety of *Lantana* plant named 'LANZ0045' substantially as illustrated and described herein.

* * * * *